(12) United States Patent
Natarajan

(10) Patent No.: US 11,661,411 B2
(45) Date of Patent: May 30, 2023

(54) QUINOXALINE COMPOUNDS AND USES THEREOF

(71) Applicant: BOARD OF REGENTS OF THE UNIVERSITY OF NEBRASKA, Lincoln, NE (US)

(72) Inventor: Amarnath Natarajan, Elkhorn, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 16/766,762

(22) PCT Filed: Dec. 3, 2018

(86) PCT No.: PCT/US2018/063587
§ 371 (c)(1),
(2) Date: May 26, 2020

(87) PCT Pub. No.: WO2019/109069
PCT Pub. Date: Jun. 6, 2019

(65) Prior Publication Data
US 2021/0002258 A1    Jan. 7, 2021

Related U.S. Application Data

(60) Provisional application No. 62/593,293, filed on Dec. 1, 2017.

(51) Int. Cl.
*C07D 403/04* (2006.01)
*A61P 35/04* (2006.01)
*A61K 9/00* (2006.01)

(52) U.S. Cl.
CPC ............ *C07D 403/04* (2013.01); *A61P 35/04* (2018.01); *A61K 9/0053* (2013.01)

(58) Field of Classification Search
CPC ...... C07D 403/04; A61P 35/04; A61K 9/0053
See application file for complete search history.

(56) References Cited

U.S. PATENT DOCUMENTS 8,993,758 B2 *  3/2015  Natarajan ............ C07D 401/12
                                                      544/353
2013/0289041 A1 * 10/2013 Natarajan ............ C07D 405/04
                                                      514/250

FOREIGN PATENT DOCUMENTS

WO    WO-2005/007099 A2    1/2005

OTHER PUBLICATIONS

McMahon et al. (2000).*
Pinedo et al. (2000).*
Baltimore, NF-kappaB is 25, Nat. Immunol., 12(8):683-5 (Jul. 2011).
Chen et al., 2,3-Substituted quinoxalin-6-amine analogs as antiproliferatives: a structure-activity relationship study, Bioorg. Med. Chem. Lett., 21(7):1929-32 (Apr. 2011).
Chen et al., Site-specific phosphorylation of IkappaBalpha by a novel ubiquitination-dependent protein kinase activity, Cell, 84(6):853-62 (Mar. 1996).
DiDonato et al., A cytokine-responsive IkappaB kinase that activates the transcription factor NF-kappaB, Nature, 388(6642):548-54 (Aug. 1997).
International Application No. PCT/US2018/063587, International Search Report and Written Opinion, dated Apr. 9, 2019.
Lee et al., Activation of the IkappaB alpha kinase complex by MEKK1, a kinase of the JNK pathway, Cell, 88(2):213-22 (Jan. 1997).
Lee et al., IKK beta suppression of TSC1 links inflammation and tumor angiogenesis via the mTOR pathway, Cell, 130(3):440-55 (Aug. 2007).
Mattson et al., NF-kappaB in neuronal plasticity and neurodegenerative disorders, J. Clin. Invest., 107(3):247-54 (Feb. 2001).
Mercurio et al., IKK-1 and IKK-2: cytokine-activated IkappaB kinases essential for NF-kappaB activation, Science, 278(5339):860-6 (Oct. 1997).
Naramura et al., Mouse Pancreatic Tumor Model Independent of Tumor Suppressor Gene Inactivation, Pancreas, 47(5):e27-e29 (May/Jun. 2018).
Pubmed Compound Summary for CID 876813, "1-(4-Methylphenyl)-3-quinoxalin-6-ylurea", U.S> National Library of Medicine, Jul. 9, 2005, 12 pp.
Radhakrishnan et al., Targeting the NF-kappaB and mTOR pathways with a quinoxaline urea analog that inhibits IKKβ for pancreas cancer therapy, Clin. Cancer Res., 19(3):2025-35 (Apr. 2013).
Rajule et al., Perturbing pro-survival proteins using quinoxaline derivatives: a structure-activity relationship study, Bioorg. Med. Chem., 20(7)2227-34 (Apr. 2012).
Sen et al., Inducibility of kappa immunoglobulin enhancer-binding protein NF-kappa B by a posttranslational mechanism, Cell, 47(6):921-8 (Dec. 1986).
Van Antwerp et al., Suppression of TNF-alpha-induced apoptosis by NF-kappaB, Science, 274(5288):787-9 (Nov. 1996).

\* cited by examiner

*Primary Examiner* — Paul V Ward
(74) *Attorney, Agent, or Firm* — Marshall, Gerstein & Borun LLP

(57) ABSTRACT

Provided herein are compounds having a structure of formula (I) and methods of using the disclosed compounds to inhibit IKKβ activity.

18 Claims, 4 Drawing Sheets

| Compound | In vitro CL (µl/min/mg protein) | $t_{1/2}$ (min) |
|---|---|---|
| 13-197 | 12.2 | 57 |
| 39-100 | 1.6 | 436 |

QUINOXALINE COMPOUNDS AND USES THEREOF

STATEMENT OF GOVERNMENT SUPPORT

This invention was made with U.S. government support under Grant No. R01 CA197999, awarded by the National Institutes of Health. The U.S. government has certain rights in the invention.

BACKGROUND

Since its discovery 25 years ago, NFκB has been shown to regulate the expression of over 200 immune, growth and inflammation genes. NFκB is constitutively active in proliferating T cells, B cells, thymocytes, monocytes and astrocytes. The clinically silent onset of pancreatic cancer ("PC") has been attributed to the upregulation of pro-inflammatory pathways such as NFκB. NFκB is constitutively active in most tumor cell lines and many tumor tissues derived from patients, but not in normal tissues. A similar observation was made in PC cell lines and pancreatic adenocarcinoma which showed constitutively activated RelA (p65 subunit of NFκB), but not in normal pancreatic tissues or immortalized/non-tumorigenic pancreatic epithelial cells. Studies also showed that PC cell lines had increased levels of NFκB subunits compared to non-malignant proliferating intestinal cells. These preclinical observations extend to PC patients: (i) High expression of RelA (NFκB subunit p65) was observed in 64% of histologically or cytologically verified locally advanced unresectable and/or metastatic PC patients and (ii) this correlates with increased expression of NFκB target genes and poor prognosis in this patient subgroup. Downregulation of NFκB (RelA) using siRNA sensitizes a subset of PC cells and pancreatic tumors in nude mice to gemcitabine. Inhibiting constitutive NFκB activity suppressed growth, angiogenesis and metastasis of PC. These observations suggest that NFκB driven pro-inflammatory pathways lead to a subset of PC's and modulating the NFκB activity is a viable therapeutic strategy for this subgroup.

The activity of IκB kinase β (IKKβ) is regulated by multiple phosphorylation events. IKKβ, like other kinases has an activation loop. Phosphorylation of two serine residues on the loop leads to the activation of IKKβ. IKKβ also has a stretch of serine residues at the C-terminus and IKKβ activation leads to auto-phosphorylation of the C-terminus serine residues. Unlike phosphorylation of the activation loop, phosphorylation of the C-terminal residues dampens kinase activity. Therefore, phosphorylation of the C-terminal serine residues not only makes IKKβ activation transient but also provides docking sites for phosphatases to dephosphorylate the serine residues on the activation loop. This suggests that IKKβ could exist in at least four distinct states as defined by its phosphorylation status and the kinase activity. The activation loop phosphorylated form of IKKβ is found in about 50% of surgical tumor specimens and in about 10% of normal tissues. Therefore, knowledge regarding the phosphorylation status of IKKβ is important from a biomarker and therapeutic development perspective. The lack of antibodies specific to the various states of IKKβ makes this a challenging problem.

A need exists for IKKβ inhibitors and methods of treating IKKβ-mediated disorders.

SUMMARY

Provided herein are compounds, or pharmaceutically acceptable salts thereof, having a structure of formula (I):

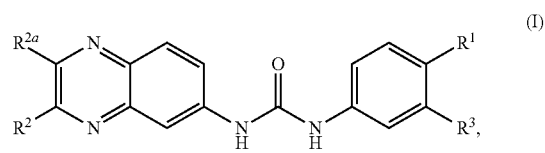

wherein $R^1$ is H, halo, $C_{1-6}$ alkyl, $C_{1-6}$ haloalkyl, $C_{1-6}$ alkoxy, $C_{1-6}$ haloalkoxy, $C_{2-6}$ haloalkenyl, $C_{2-6}$ haloalkynyl, $C_{6-10}$ aryl or 5-7 membered heteroaryl having 1-4 ring heteroatoms selected from N, O, and S; one of $R^2$ and $R^{2a}$ is a 5-membered heteroaryl having 1-4 ring heteroatoms independently selected from N, O, and S, and optionally substituted with 1-4 $R^4$ groups and the other is H; $R^3$ is H, halo, $C_{1-6}$ alkyl, $C_{1-6}$ alkoxy, $C_{1-6}$ haloalkoxy, $C_{1-6}$ haloalkyl, $C_{2-6}$ haloalkenyl, or $C_{2-6}$ haloalkynyl; each $R^4$ is independently halo, $C_{1-6}$ alkyl, $C_{1-6}$ haloalkyl, $C_{1-6}$ alkoxy, $C_{2-6}$ haloalkenyl, $C_{2-6}$ haloalkynyl, or $C_{6-10}$ aryl; any $C_{1-6}$ alkyl or $C_{6-10}$ aryl of $R^1$ and $R^4$ can optionally be substituted with 1-3 groups selected from halo, OH, $C_{1-6}$ alkyl, $C_{1-6}$ haloalkyl, CN, $OC_{1-6}$ alkyl, $CO_2H$, and $CO_2C_{1-6}$ alkyl; and with the proviso only one of $R^1$ and $R^3$ can be H.

Further provided herein are pharmaceutical compositions comprising a compound or salt disclosed herein and a pharmaceutically acceptable excipient.

Also provided herein are methods of decreasing inhibitor of kappa B kinase β (IKKβ) activity in a cell comprising contacting the cell with a compound or salt as disclosed herein, in an amount effective to decrease activity of IKKβ. In embodiments, the compound or salt also decreases activity of NFκB.

Also provided herein are methods of treating a disorder associated with aberrant inhibitor of kappa B kinase β (IKKβ) activity in a subject comprising administering to the subject a therapeutically effective amount of a compound or salt as disclosed herein.

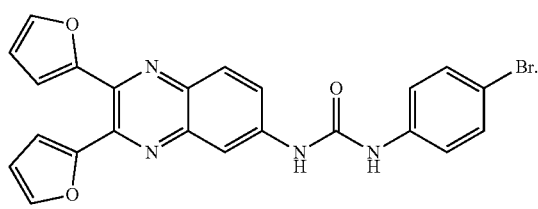 [SMILES: O=C(Nc1ccc(Br)cc1)Nc1ccc2nc(-c3ccco3)c(-c3ccco3)nc2c1]

Compound 39-100 has a structure:

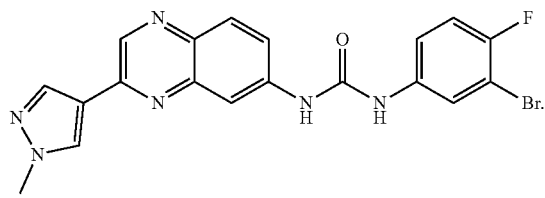 [SMILES: Cn1cc(-c2cnc3ccc(NC(=O)Nc4ccc(F)c(Br)c4)cc3n2)cn1]

ML-120B has a structure:

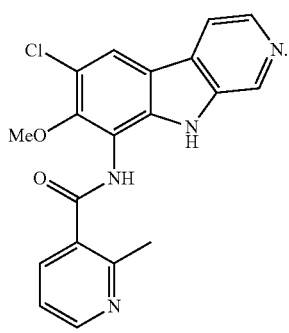 [SMILES: COc1c(Cl)cc2c([nH]c3cnccc32)c1NC(=O)c1cccnc1C]

Figure 2:
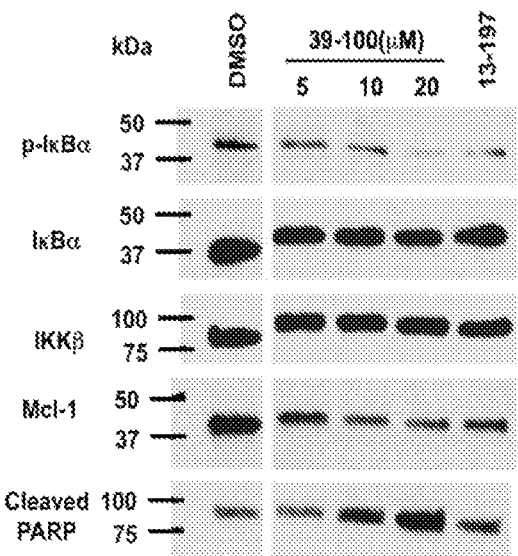

FIG. 2 shows a western blot analyses with compound 39-100 in comparison with compound 13-197.

Figure 3:
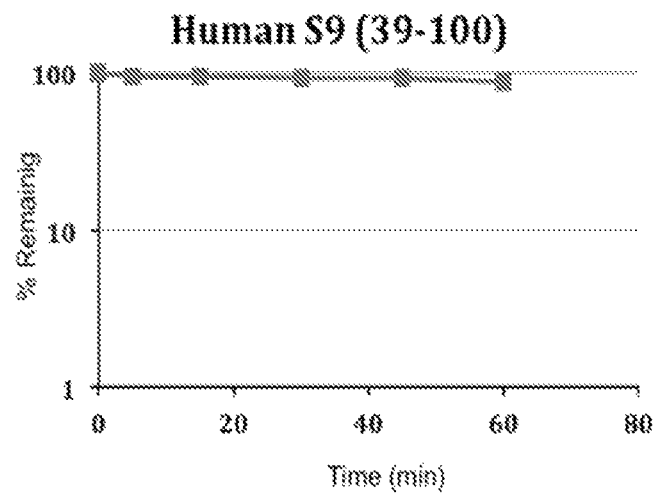

FIG. 3 shows in-vitro metabolic stability profile of compound 39-100 in human liver S9 fraction.

Figure 4:
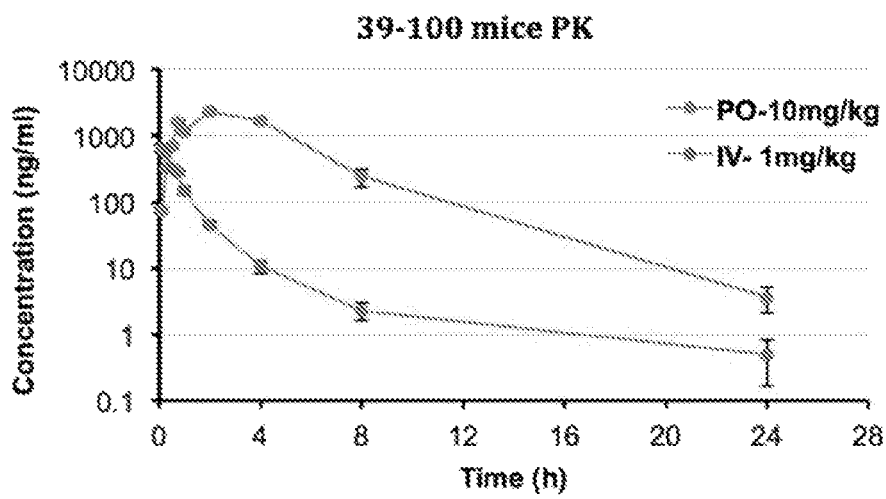

FIG. 4 shows plasma concentration vs. time profile of compound 39-100 after 1 mg/kg intravenous (IV) an d10 mg/kg oral (PO) dose administration in mice (N=5, Mean±SEM)

Figure 5:
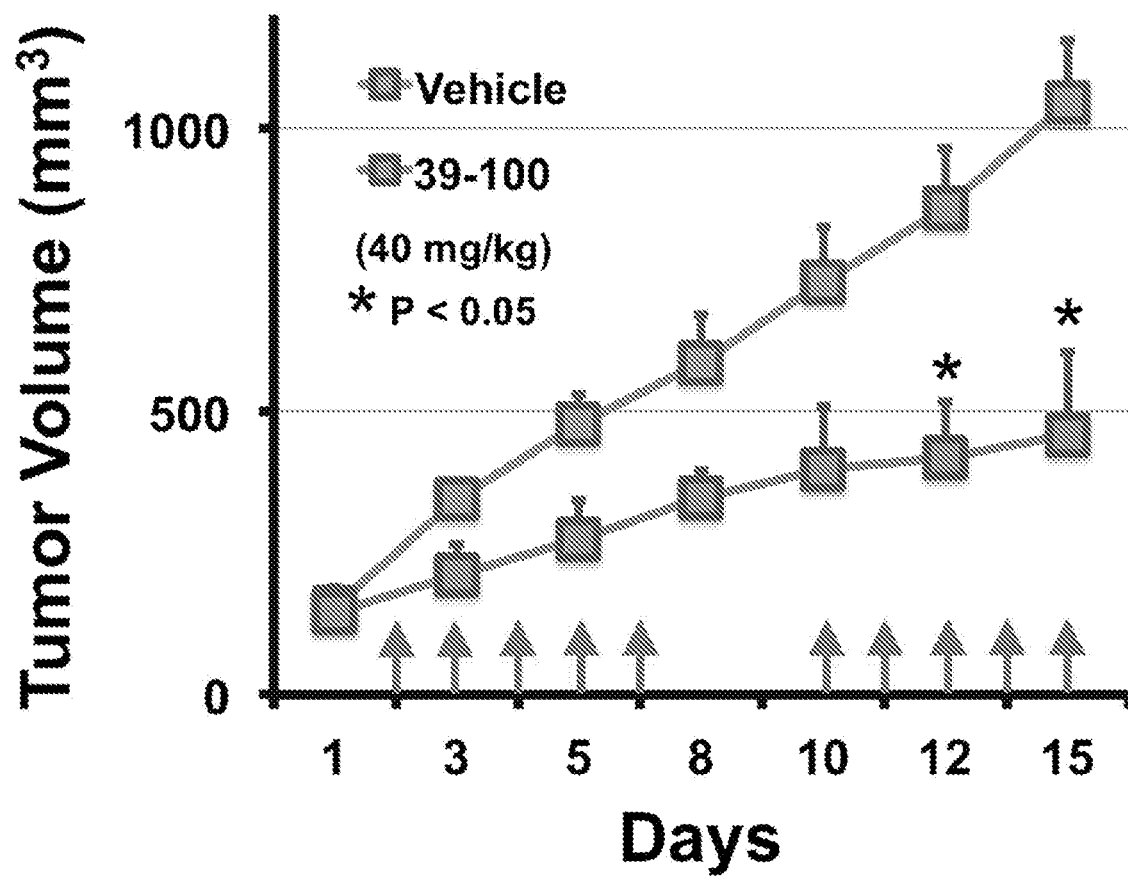

FIG. 5 shows a two-week colon tumor growth inhibition study with compound 39-100.

Figure 6:
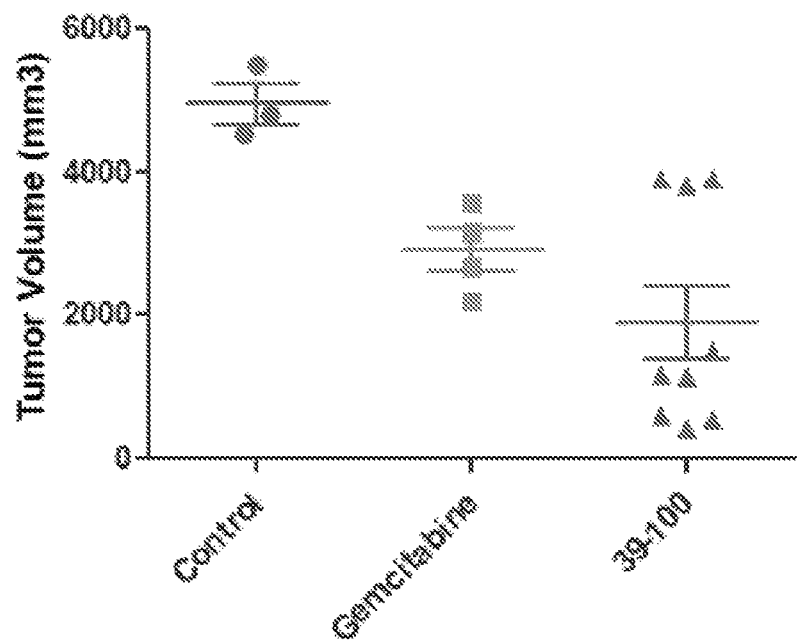

FIG. 6 shows change in tumor volume in a syngenetic orthotopic pancreatic cancer model in mice after a four-week treatment of gemcitabine or compound 39-100 compared to control.

Figure 7:
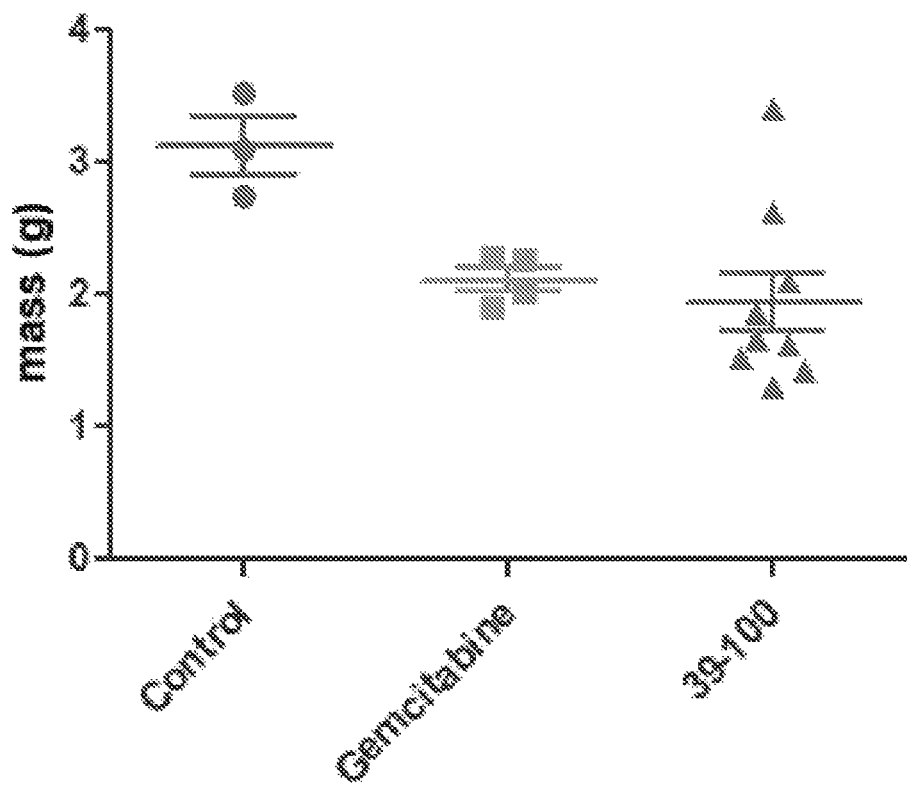

FIG. 7 shows change in tumor mass in a syngenetic orthotopic pancreatic cancer tumor model in mice after a four-week treatment of gemcitabine or compound 39-100 compared to control.

DETAILED DESCRIPTION

Provided herein are compounds having the structure of formula (I) or salts thereof ("compound (I)"), methods of inhibiting IKKβ and methods of treating a disorder associated with aberrant inhibitor of IKKβ activity in a subject.

The compounds disclosed herein have a structure of formula (I) or a pharmaceutically acceptable salt thereof:

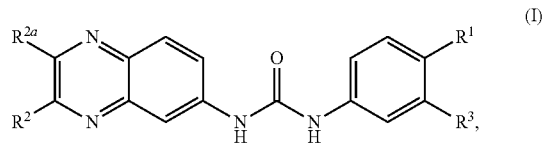

(I)

wherein $R^1$ is H, halo, $C_{1-6}$ alkyl, $C_{1-6}$ haloalkyl, $C_{1-6}$ alkoxy, $C_{1-6}$ haloalkoxy, $C_{1-6}$ haloalkenyl, $C_{1-6}$ haloalkynyl, $C_{6-10}$ aryl or 5-7 membered heteroaryl having 1-4 ring heteroatoms selected from N, O, and S; one of $R^2$ and $R^{2a}$ is a 5-membered heteroaryl having 1-4 ring heteroatoms independently selected from N, O, and S, and optionally substituted with 1-4 $R^4$ groups and the other is H; $R^3$ is H, halo, $C_{1-6}$alkyl, $C_{1-6}$ alkoxy, $C_{1-6}$ haloalkoxy, $C_{1-6}$haloalkyl, $C_{1-6}$haloalkenyl, or $C_{1-6}$haloalkynyl; each $R^4$ is independently halo, $C_{1-6}$ alkyl, $C_{1-6}$ haloalkyl, $C_{1-6}$ alkoxy, $C_{1-6}$ haloalkenyl, $C_{1-6}$ haloalkynyl, or $C_{6-10}$ aryl; any $C_{1-6}$alkyl or $C_{6-10}$aryl of $R^1$ and $R^4$ can optionally be substituted with 1-3 groups selected from halo, OH, $C_{1-6}$alkyl, $C_{1-6}$haloalkyl, CN, $OC_{1-6}$alkyl, $CO_2H$, and $CO_2C_{1-6}$alkyl; and with the proviso only one of $R^1$ and $R^3$ can be H.

In various embodiments herein, $R^1$ is H, halo, $C_{1-6}$alkyl, or $C_{1-6}$haloalkyl. In some cases, $R^1$ is F, Br, phenyl, $CF_2H$, $CFH_2$ or $CF_3$. In various embodiments, $R^1$ is F.

In some embodiments, $R^2$ is a 5-membered heteroaryl having 1-4 ring heteroatoms selected from N, O, and S and is substituted with 1-4 $R^4$ groups. In embodiments, $R^2$ is furanyl, thiophenyl, or pyrazolyl and optionally substituted with 1-4 $R^4$ groups. In some cases, $R^2$ is substituted with 1-2 $R^4$ groups. In various cases, $R^2$ is pyrazolyl and substituted with 1-4 $R^4$ groups. In some cases, $R^2$ is

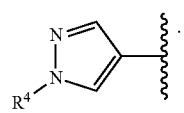

In some embodiments, $R^{2a}$ is a 5-membered heteroaryl having 1-4 ring heteroatoms selected from N, O, and S and is substituted with 1-4 $R^4$ groups. In embodiments, $R^{2a}$ is furanyl, thiophenyl, or pyrazolyl and optionally substituted with 1-4 $R^4$ groups. In some cases, $R^{2a}$ is substituted with 1-2 $R^4$ groups. In various cases, $R^{2a}$ is pyrazolyl and substituted with 1-4 $R^4$ groups. In some cases, $R^{2a}$ is

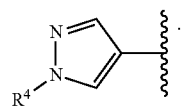

In embodiments, $R^3$ is halo, $C_{1-6}$alkyl, or $C_{1-6}$haloalkyl. In embodiments, $R^3$ is Br, F, $CH_3$, $CF_2H$, $CFH_2$, or $CF_3$. In embodiments, $R^3$ is Br or $CF_3$. In various embodiments, at least one $R^4$ is $C_{1-6}$alkyl or $C_{1-6}$haloalkyl. In some embodiments, at least one $R^4$ is F, Br, Cl, methyl, methoxy, ethyl, or $CF_3$. In some cases, $R^4$ is methyl or $CF_3$. In some embodiments, compound (I) is in the form of a salt.

Some specifically contemplated compounds of Formula (I) include

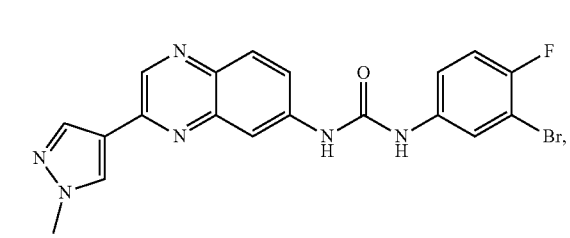

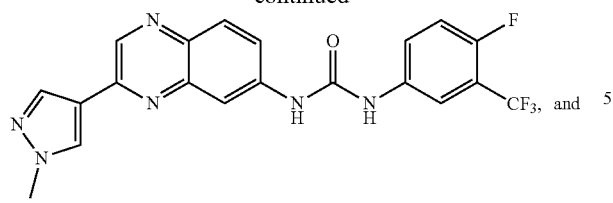

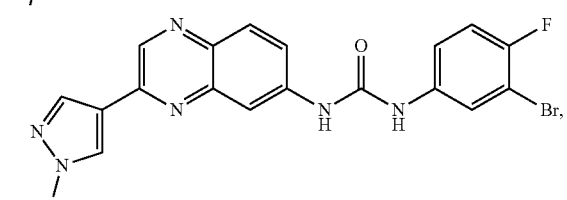

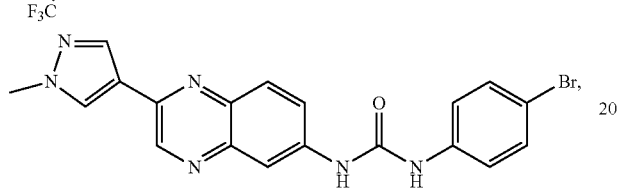

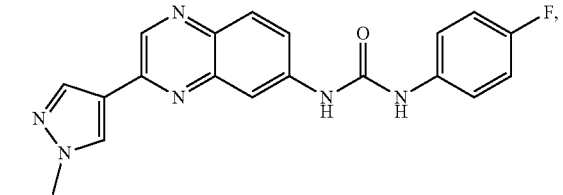

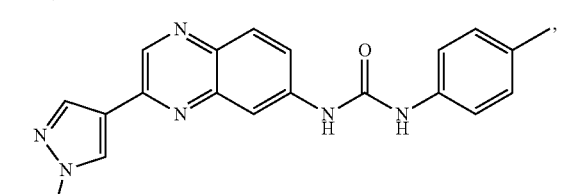

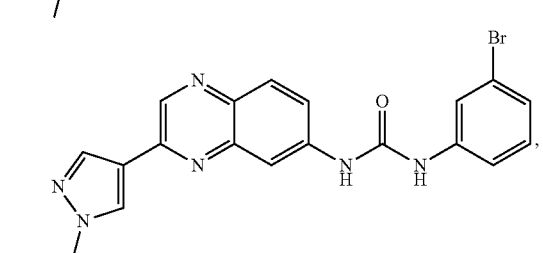

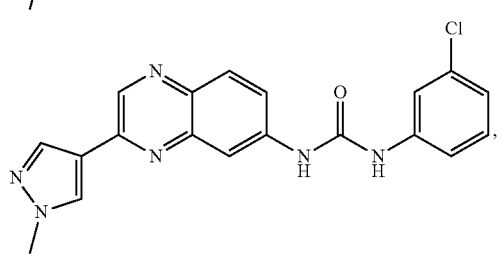

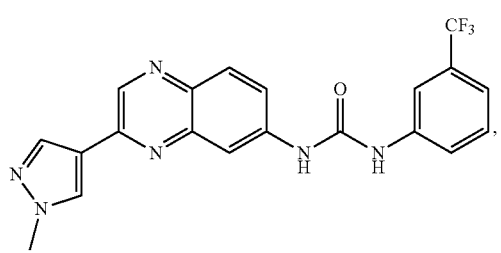

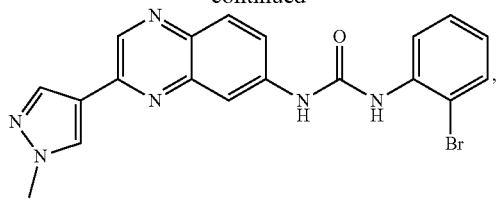

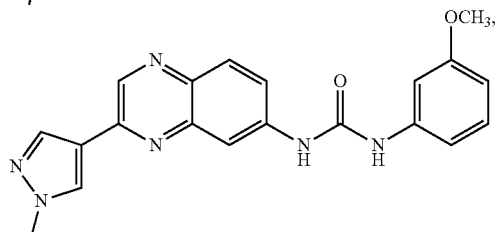

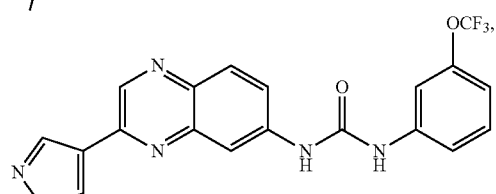

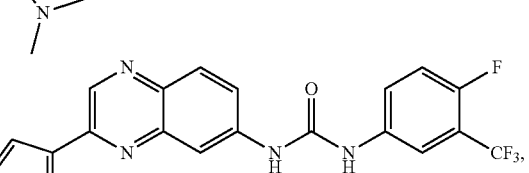

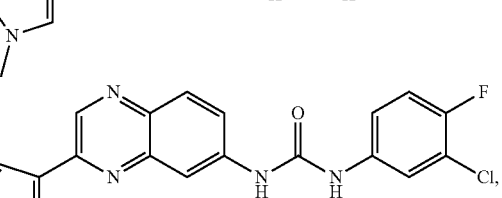

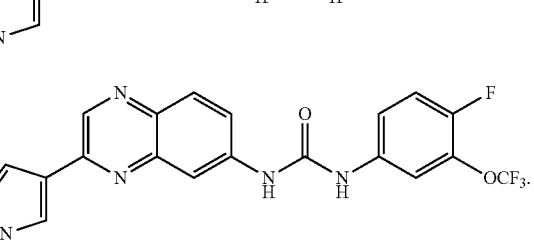

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_{1-6}$ alkyl refers to an alkyl group having a number of carbon atoms encompassing the entire range (e.g., 1 to 6 carbon atoms), as well as all subgroups (e.g., 1-5, 2-6, 1-4, 3-6, 1, 2, 3, 4, 5, and 6 carbon atoms). Nonlimiting examples of alkyl groups include, methyl, ethyl, n-propyl, isopropyl, n-butyl, sec-butyl (2-methylpropyl), t-butyl (1,1-dimethylethyl), and hexyl. Unless otherwise indicated, an alkyl group can be an unsubstituted alkyl group or a substituted alkyl group.

As used herein, the term "haloalkyl" refers to an alkyl group substituted with one or more halogen atoms. Specifically contemplated is an alkyl group with one or more fluorine atoms, for example $CH_2F$, $CHF_2$, or $CF_3$. In various cases, the haloalkyl group can be perhalogenated (i.e., all hydrogen atoms are substituted with a halo atom), such as $CF_3$, $CF_2CF_3$, or $CF_2CF_2CF_3$.

As used herein, the term "alkenyl" is defined identically as "alkyl" except for containing at least one carbon-carbon double bond, and having two to thirty carbon atoms, for example, two to twenty carbon atoms, or two to ten carbon atoms. The term $C_n$ means the alkenyl group has "n" carbon atoms. For example, $C_4$ alkenyl refers to an alkenyl group that has 4 carbon atoms. $C_{2-7}$ alkenyl refers to an alkenyl group having a number of carbon atoms encompassing the entire range (e.g., 2 to 6 carbon atoms), as well as all subgroups (e.g., 2-5, 2-4, 3-6, 2, 3, 4, 5, and 6 carbon atoms). Specifically contemplated alkenyl groups include ethenyl, 1-propenyl, 2-propenyl, and butenyl. Unless otherwise indicated, an alkenyl group can be an unsubstituted alkenyl group or a substituted alkenyl group.

As used herein, the term "haloalkenyl" refers to an alkenyl group substituted with one or more halogen atoms. Specifically contemplated is an alkenyl group with one or more fluorine atoms. The alkenyl group can be perhalogenated.

As used herein, the term "alkynyl" is defined identically as "alkyl" except for containing at least one carbon-carbon triple bond, and having two to thirty carbon atoms, for example, two to twenty carbon atoms, or two to ten carbon atoms. The term $C_n$ means the alkynyl group has "n" carbon atoms. For example, $C_4$ alkynyl refers to an alkynyl group that has 4 carbon atoms. $C_{2-6}$ alkynyl refers to an alkynyl group having a number of carbon atoms encompassing the entire range (e.g., 2 to 6 carbon atoms), as well as all subgroups (e.g., 2-5, 2-4, 3-6, 2, 3, 4, 5, and 6 carbon atoms). Specifically contemplated alkynyl groups include ethynyl, 1-propynyl, 2-propynyl, and butynyl. Unless otherwise indicated, an alkynyl group can be an unsubstituted alkenyl group or a substituted alkenyl group.

As used herein, the term "haloalkynyl" refers to an alkynyl group substituted with one or more halogen atoms. Specifically contemplated is an alkynyl group with one or more fluorine atoms. The alkynyl group can be perhalogenated.

As used herein, the term "aryl" refers to a cyclic aromatic group, such as a monocyclic aromatic group, e.g., phenyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. $C_{6-10}$ aryl group is an aryl group that has 6-10 ring carbon atoms. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a cyclic aromatic ring having five to twelve total ring atoms (e.g., a monocyclic aromatic ring with 5-7 total ring atoms), and containing one to four heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Heteroaryl groups can be isolated (e.g., pyridyl) or fused to another heteroaryl group (e.g., purinyl), a cycloalkyl group (e.g., tetrahydroquinolinyl), a heterocycloalkyl group (e.g., dihydronaphthyridinyl), and/or an aryl group (e.g., benzothiazolyl and quinolyl). Examples of heteroaryl groups include, but are not limited to, thienyl, furyl, pyridyl, pyrrolyl, pyrazolyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl. When a heteroaryl group is fused to another heteroaryl group, then each ring can contain five to seven total ring atoms and one to four heteroatoms in its aromatic ring.

A used herein, the term "substituted," when used to modify a chemical functional group, unless noted otherwise, refers to the replacement of at least one hydrogen radical on the functional group with a substituent. Substituents can include, but are not limited to, alkyl, cycloalkyl, alkynyl, heterocycloalkyl, thioether, polythioether, aryl, heteroaryl, hydroxyl, oxy, alkoxy, heteroalkoxy, aryloxy, heteroaryloxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

The term "alkoxy" used herein refers to an —Oalkyl group. The term "haloalkoxy" used herein refers to an —Ohaloalkyl group.

The salts, e.g., pharmaceutically acceptable salts, of compound (I) may be prepared by reacting the appropriate base or acid with a stoichiometric equivalent of compound (I).

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include anions, for example sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, and mandelate. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Specifically contemplated compounds of the disclosed Formula (I) include

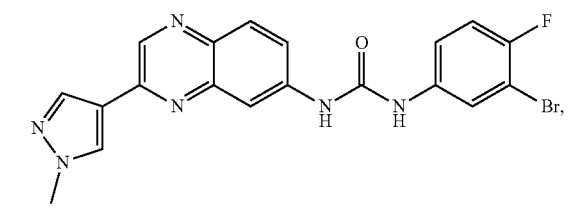

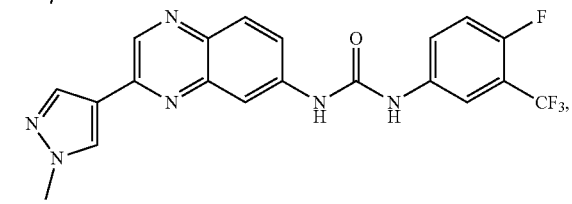

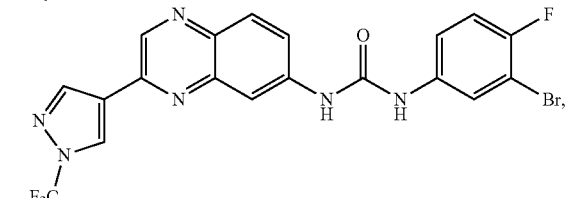

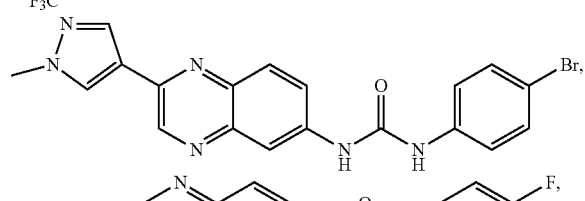

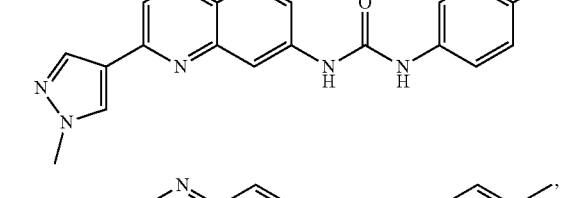

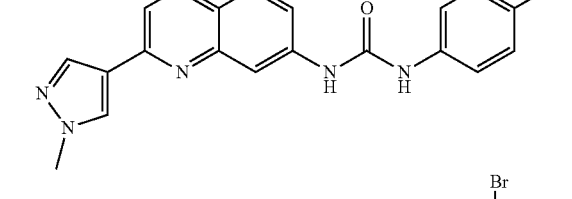

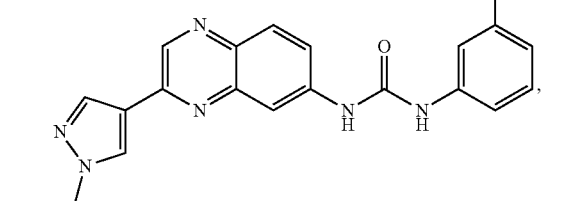

-continued

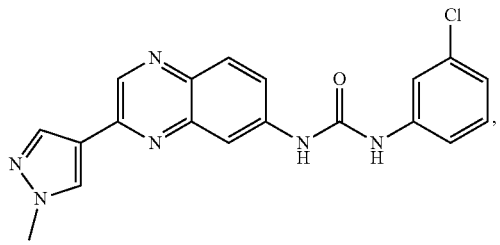

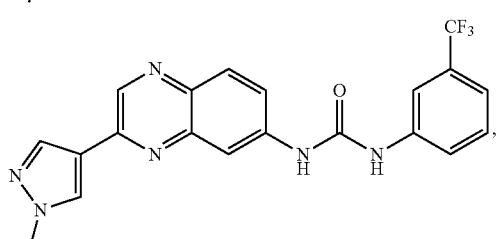

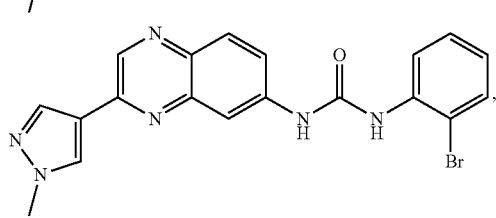

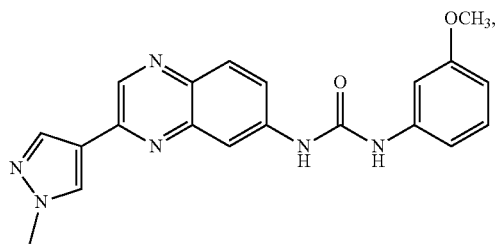

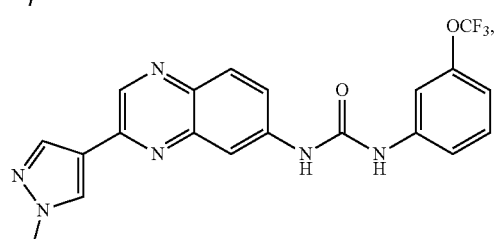

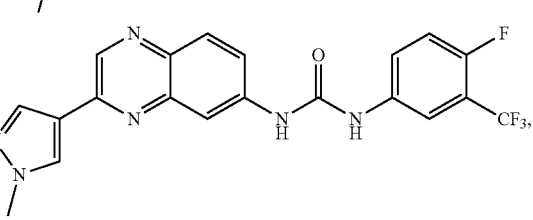

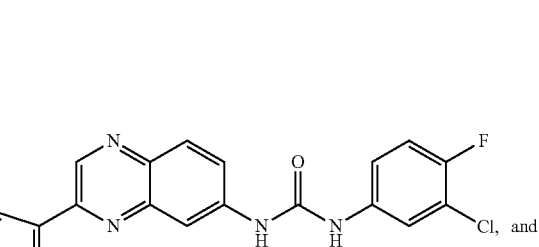

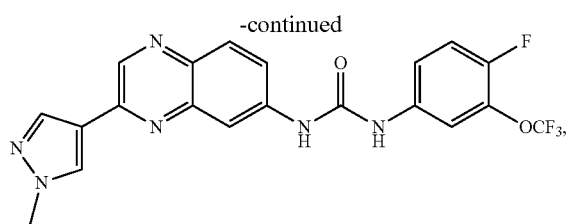

or a pharmaceutically salt thereof. Also contemplated are compounds having a structure shown in Table 1 below.

TABLE 1

| ID# | —R₁ | —R₂ |
|---|---|---|
| 39-061 | 4-(1-methyl)-1H-Pyrazole | H |
| 39-055 | H | 4-(1-methyl)-1H-Pyrazole |
| 39-072 | 3-(1-methyl)-1H-Pyrazole | H |
| 39-062 | H | 3-(1-methyl)-1H-Pyrazole |
| 39-09D | H | 4-1H-Pyrazole |
| 39-077 | H | 4-(1,3-dimethyl)-1H-Pyrazole |

| ID# | X | R₁ | R₂ | R₃ |
|---|---|---|---|---|
| 39-076 | CH₂ | Br | H | H |
| 39-071 | NH | H | H | H |
| 39-066 | NH | F | H | H |
| 39-085 | NH | CH₃ | H | H |
| 39-084 | NH | NO₂ | H | H |
| 39-086 | NH | H | Br | H |
| 39-102 | NH | H | H | Br |
| 42-064 | NH | H | Cl | H |
| 42-066 | NH | H | CH₃ | H |
| 42-071 | NH | H | CF₃ | H |
| 42-076 | NH | H | OCH₃ | H |
| 42-81B | NH | H | OCF₃ | H |

| ID# | X | R |
|---|---|---|
| 39-100 | N | Br |
| 42-062 | N | CF₃ |
| 42-065 | N | Cl |
| 42-074 | N | CH₃ |
| 42-078 | N | OCH₃ |
| 42-096 | N | OCF₃ | disclosed herein inhibit the NFκB pathway and/or the mTOR pathway. In one embodiment, provided is a method of decreasing inhibitor of IKKβ activity in cells comprising contacting the cell with the compound or salt of structural formula (I) in an amount effective to decrease activity of IKKβ. In a further embodiment, the method decreases activity of NFκB. In some cases, provided herein is a method of treating a disorder associated with aberrant inhibitor of IKKβ activity in a subject comprising administering to the subject a therapeutically effective amount of a compound of structural formula (I). In some cases, the disorder is cancer, an autoimmune disease, an inflammatory disease, diabetes, cardiovascular disease, or a neurological disease.

As used herein, the terms "treat," "treating," "treatment," and the like refer to eliminating, reducing, or ameliorating a Therapeutic Methods Provided herein are IKKβ inhibitors, as exemplified by compounds of structural formula (I), for the treatment of a variety of diseases and conditions wherein inhibition of IKKβ has a beneficial effect. In some cases, the compounds disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of structural formula (I) to an individual in need of such treatment.

The term "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The compounds described herein therefore can be used to treat a variety of diseases and conditions where modulation (e.g., inhibition or activation) of IKKβ, NFκB pathway and/or the mTOR pathway provides a benefit. Examples of such diseases and condition include, but are not limited to cancer, diabetes, an autoimmune disease, an inflammatory disease, cardiovascular disease, and a neurological disease.

The disclosed methods are useful for treating cancer, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "cancer resistance" refers to an improved capacity of a subject to resist cancer growth, in particular growth of a cancer already had. In other words, the term "cancer resistance" refers to a decreased propensity for cancer growth in a subject.

In some aspects, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. In another aspect, methods of treatment are presented herein to treat cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatis, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may be targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Hürthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may be targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plamsa cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestimal cancers that may be targeted include extrahepatic bile duct cancer, colon cancer, colon and rectum cancer, colorectal cancer, gallbladder cancer, gastric (stomach) cancer, gastrointestinal carcinoid tumor, gastronintestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer à deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenstrom's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

Specific cancers contemplated include acute lymphoblastic leukemia (ALL); acute myeloid leukemia (AML), adrenocortical carcinoma, AIDS-related cancer, Kaposi sarcoma, lymphoma, anal cancer, appendix cancer, astrocytomas, atypical teratoid/rhabdoid tumor, basal cell carcinoma, bile duct cancer, bladder cancer, bone cancer, osteosarcoma, malignant fibrous histiocytoma, brain stem glioma, brain tumor, astrocytoma, brain and spinal cord tumor, brain stem glioma, CNS atypical teratoid/rhabdoid tumor, CNS embryonal tumor, craniopharyngioma, ependymoblastoma, ependymoma, medulloblastoma, medulloepithelioma, pineal parenchymal tumor, supratentorial primitive neuroectodermal tumor, pineoblastoma, breast cancer, bronchial tumor, Burkitt lymphoma, non-Hodgkin lymphoma, carcinoid tumor, cervical cancer, chordoma, chronic lymphocytic leukemia (CLL), chronic myelogenous leukemia (CML), chronic myeloproliferative disorder, colon cancer, colorectal cancer, craniopharyngioma, cutaneous T-cell lymphoma, embryonal tumor, endometrial cancer, ependymoblastoma, ependymoma, esophageal cancer, esthesioneuroblastoma, Ewing sarcoma, extracranial germ cell tumor, extragonadal germ cell tumor, eye cancer, intraocular melanoma, retinoblastoma, gallbladder cancer, gastric (stomach) cancer, gastrointestinal carcinoid tumor, gastrointestinal stromal tumor (GIST), gestational trophoblastic tumor, glioma, hairy cell leukemia, head and neck cancer, heart cancer, hepatocellular (liver) cancer, histiocytosis, langerhans cell, Hodgkin lymphoma, hypopharyngeal cancer, intraocular melanoma, islet cell tumor, renal cell cancer, langerhans cell histiocytosis, laryngeal cancer, leukemia, lip and oral cavity cancer, liver cancer, lobular carcinoma in situ (LCIS), lung cancer, lymphoma, macroglobulinemia, medulloblastoma, medulloepithelioma, melanoma, Merkel cell carcinoma, mesothelioma, metastatic squamous neck cancer, mouth cancer, multiple endocrine neoplasia syndrome, multiple myeloma/plasma cell neoplasm, mycosis fungoide, myelodysplastic syndrome, myelodysplastic/myeloproliferative neoplasm, nasal cavity and paranasal sinus cancer, nasopharyngeal cancer, neuroblastoma, non-small cell lung cancer, oral cancer, oropharyngeal cancer, ovarian cancer, pancreatic cancer, papillomatosis, paraganglioma, parathyroid cancer, penile cancer, pharyngeal cancer, pheochromocytoma, pineal parenchymal tumor, pituitary tumor, plasma cell neoplasm, pleuropulomary blastoma, prostate cancer, rectal cancer, renal pelvis and ureter transitional cell cancer, retinoblastoma, rhabdomyosarcoma, salivary gland cancer, sarcoma, uterine sarcoma, soft tissue sarcoma, skin cancer, small cell lung cancer, small intestines cancer, squamous cell carcinoma, stomach cancer, T-cell lymphoma, testicular cancer, throat cancer, thymoma, thymic cancer, thyroid cancer, gestational trophoblastic cancer, vaginal cancer, vulvar cancer, Wilms tumor, and Waldenstrom macroglobulinemia. Specific cancers contemplated include pancreatic cancer, lymphoma, leukemia, colon cancer, colorectal cancer, familial adenomatous polyposis (FAP), hereditary non-polyposis cancer (HNPCC), colitis-associated cancer, gastric cancer, and breast cancer. Specific inflammatory diseases contemplated include arthritis, rheumatoid arthritis, osteoarthritis, atherosclerosis, multiple sclerosis, chronic inflammatory demyelinating polyradiculoneuritis, asthma, inflammatory bowel disease, helicobacter pylon-associated gastritis, Crohn's disease, ulcerative colitis, and systemic inflammatory response syndrome.

The disclosed methods herein are useful for treating neurological disorders. For example, the NFκB pathway is involved in various central nervous system (CNS) diseases such as ischemic stroke, traumatic brain injury, seizures, and neurodegenerative disorders. Non-limiting examples of neurodegenerative disorders include Alzheimer's Disease, Parkinson's Disease, ALS, and Huntington's. The role of the NFκB pathway in CNS disease is described in greater detail in Mattson et al., *J. Clinical Invest.,* 107(3):247 (2001).

The term "autoimmune disease" is used throughout the specification to refer to a pathogenic condition in which the patient's immune system results in disease from a self antigen (autoimmunity) or a foreign antigen (immune dysfunction/dysregulation or immune inflammatory disease). Autoimmunity is present in everyone to some extent. It is usually harmless and probably a universal phenomenon of vertebrate life. However, autoimmunity can be the cause of a broad spectrum of human illnesses, known as autoimmune diseases. This concept of autoimmunity as the cause of human illness is relatively new, and it was not accepted into the mainstream of medical thinking until the 1950s and 1960s. Autoimmune diseases are, thus, defined when the progression from benign autoimmunity to pathogenic autoimmunity occurs. This progression is determined by both genetic influences and environmental triggers. The concept of autoimmunity as the actual cause of human illness (rather than a consequence or harmless accompaniment) can be used to establish criteria that define a disease as an autoimmune disease. Autoimmune diseases or diseases which are characterized as involving immune dysfunction or disregulation (immune inflammatory disease), which may be treated by the present invention include systemic lupus erythematosis (SLE), diabetes mellitus (type I), asthma, ulcerative cholitis, Grave's disease, arthritis, including rheumatoid arthritis and osteoarthritis, pernicious anemia, and multiple sclerosis, among numerous others. Numerous autoimmune diseases may be treated using the method of the present invention including autoimmune blood diseases, including pernicious anemia, autoimmune hemolytic anemia, aplastic anemia, idiopathic thrombocytopenic purpura, ankylosing spondilitis; autoimmune diseases of the musculature including polymyositis and dermatomyositis, autoimmune diseases of the ear including autoimmune hearing loss and Meniere's syndrome, autoimmune eye diseases, including Mooren's disease, Reiter's syndrome and Vogt-Koyanagi-Harada disease, autoimmune diseases of the kidney including glomerulonephritis and IgA nephropathy; diabetes mellitus (type I); autoimmune skin diseases including pemphigus (autoimmune bullous diseases), such as pemphigus vulgaris, pemphigus foliaceus, pemphigus erythematosus, bullous pemphigoid, vitiligo, epidermolysis bullosa acquisita, psoriasis and alopecia greata; cardiovascular autoimmune diseases, including autoimmune myocarditis, vasculitis including Churg-Strauss syndrome, giant cells arteritis, Kawasaki's disease, polyarteritis nodosa, Takayasu's arteritis and Wegener's granulomatosis; endocrine autoimmune diseases, including Addison's disease, autoimmune hypoparathyroidism, autoimmune hypophysitis, autoimmune oophoritis, autoimmune orchitis, Grave's Disease, Hashimoto's thyroiditis, polyglandular autoimmune syndrome type 1 (PAS-I) polyglandular autoimmune syndrome type 2 (PAS-2), and polyglandular autoimmune syndrome type 3 (PAS-3); autoimmune gastroenteric diseases including autoimmune hepatitis, primary biliary cirrhosis, inflammatory bowel disease, celiac disease, Crohn's disease; autoimmune nervous diseases, including multiple sclerosis, myasthenia gravis, Guillan-Barre syndrome and chronic inflammatory demyelinating neuropathy; and systemic autoimmune diseases including systemic lupus erythematosus, antiphospholid syndrome, autoimmune lymphoproliferative disease, autoimmune polyendocrinopathy, Bechet's disease, Goodpasture's disease, arthritis, including rheumatoid arthritis, osteoarthritis and septic arthritis, sarcoidosis, scleroderma and Sjogren's syndrome and psoriasis among others.

As used herein, "inflammatory diseases" refers to diseases, disorders and conditions, that are mediated by VCAM-1 and/or IL-6. Exemplary inflammatory diseases, include, but are not limited to, arthritis, asthma, dermatitis, psoriasis, cystic fibrosis, post transplantation late and chronic solid organ rejection, multiple sclerosis, systemic lupus erythematosus, inflammatory bowel diseases, autoimmune diabetes, diabetic retinopathy, diabetic nephropathy, diabetic vasculopathy, ocular inflammation, uveitis, rhinitis, ischemic-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, and small artery disease.

As used herein, "cardiovascular disease" (CVD) is used to classify numerous conditions that affect the heart, heart valves, blood, and vasculature of the body, including coronary artery disease (CAD). Cardiovascular diseases include, but are not limited to, endothelial dysfunction, coronary artery disease, carotid artery disease, angina pectoris, myocardial infarction, atherosclerosis, congestive heart failure, hypertension, cerebrovascular disease, stroke, transient ischemic attacks, deep vein thrombosis, peripheral artery disease, cardiomyopathy, arrhythmias, aortic stenosis, and aneurysm. Such diseases frequently involve atherosclerosis.

Presented herein is a method of administering compound (I) or salt thereof as the neat compound or as a pharmaceutical composition orally, intravenously, or parenterally. In some cases, the compound having a structure of formula (I) or salt thereof is administered orally. Administration of a pharmaceutical composition, or neat compound of structural formula (I), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I) and, optionally, a second therapeutic agent useful in the treatment of diseases and conditions wherein inhibition of IKKβ provides a benefit, packaged separately or together, and an insert having instructions for using these active agents.

Dosing and Pharmaceutical Formulations

The term "therapeutically effective amount," as used herein, refers to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein or known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 1 mg/kg to about 50 mg/kg, about 1 mg/kg to about 40 mg/kg, and about 5 mg/kg to about 30 mg/kg.

A compound of structural formula (I) used in a method described herein can be administered in an amount of about 0.005 to about 750 milligrams per dose, about 0.05 to about 500 milligrams per dose, or about 0.5 to about 250 milligrams per dose. For example, a compound of structural formula (I) can be administered, per dose, in an amount of about 0.005, 0.05, 0.5, 1, 2, 3, 4, 5, 10, 15, 20, 30, 40, 50, 100, 150, 200, 250, 300, 350, 400, 450, 500, 550, 600, 650, 700, or 750 milligrams, including all doses between 0.005 and 750 milligrams.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of a disorder as disclosed herein (e.g., an anticancer agent or an anti-inflammatory agent).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound described herein.

Synthesis of Compounds

The compounds disclosed herein can be synthesized through any means available to the synthetic chemist and in view of the guidance of the schemes below. Non-limiting examples for preparing compounds disclosed herein is provided below.

Scheme 1

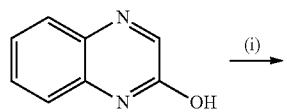

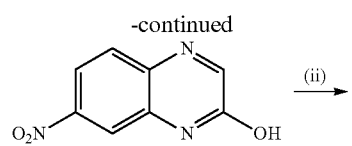

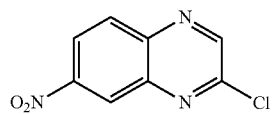

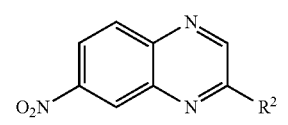

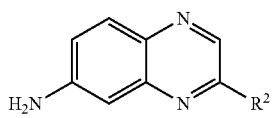

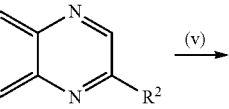

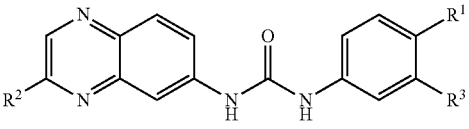

Exemplary reagents and conditions for reactions of Scheme 1 are: (i) Acetic acid, conc. $HNO_3$, rt, 24 h; (ii) $PCl_5$, $POCl_3$, 110° C., 4 h; (iii) heteroarylborane or heteroarylborate, $Pd(PPh_3)_4$, $Na_2CO_3$, DMF-Dioxane (1:1), 100° C., 20 h; (iv) Pd/C, $H_2$, 18 h; (v) can be (a) triphosgene, $CH_2Cl_2$: THF (4:1), DIPEA, 0° C.-rt, 14 h; (b) 3—$R^3$—4—$R^1$-aniline, DIPEA, $CH_2Cl_2$, 0° C-rt, 12 h; or (v) can be 1—$R^1$—4-isocyanato-2—$R^3$-benzene, $CH_2Cl_2$, rt, 48 h. Compounds as disclosed herein can be prepared by the method noted in the above scheme.

Further provided herein are detailed exemplary embodiments of examples. They should, however, not be construed as limiting the scope. All citations throughout the disclosure are hereby expressly incorporated by reference.

EXAMPLES

Preparation of Compounds Herein
Experimental Methods:

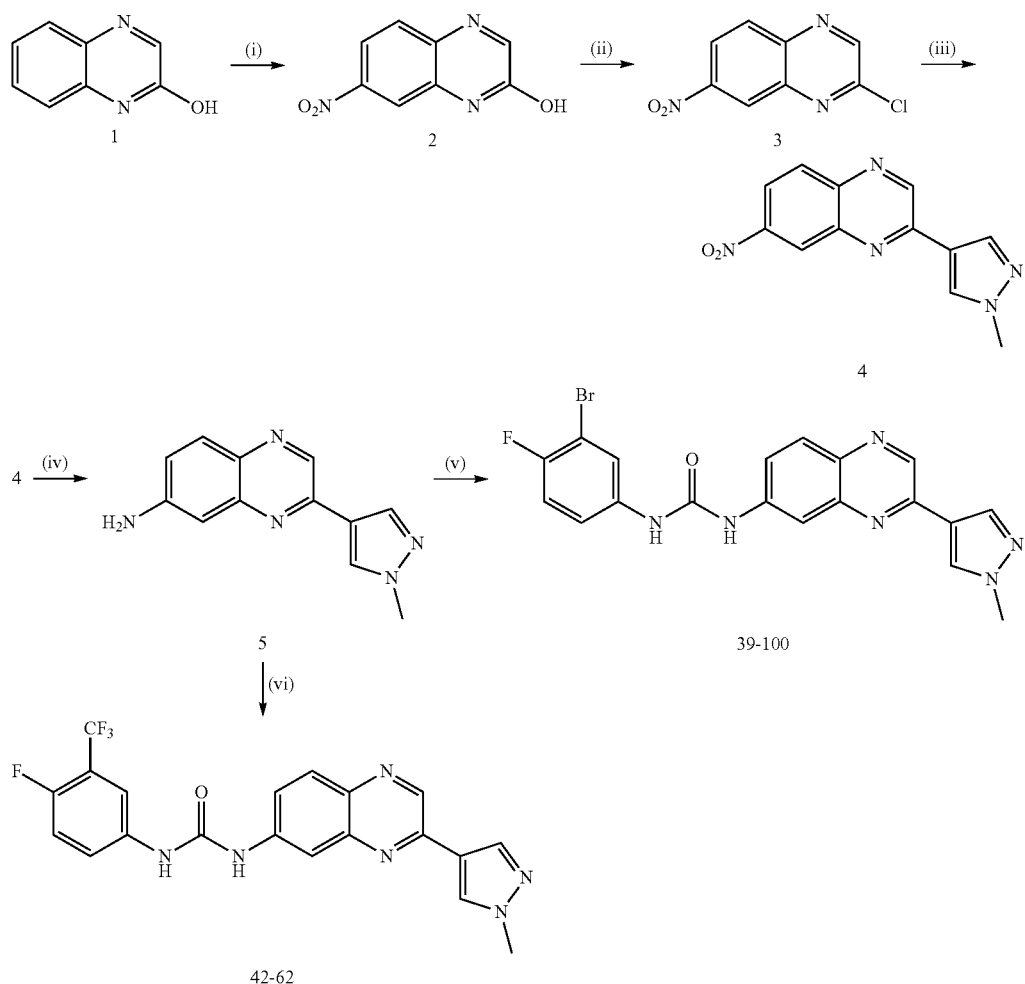

Reagents and conditions: (i) Acetic acid, conc. HNO₃, rt, 24 h, 85%; (ii) PCl₅, POCl₃, 110° C., 4 h, 96%; (iii) 1-Methyl-4-(4,4,5,5-tetramethyl-1,3,2-dioxaborolan-2-yl)-1H-pyrazole, Pd(PPh₃)₄, Na₂CO₃, DMF-Dioxane (1:1), 100° C., 20 h, 82%; (iv) Pd/C, H₂, 18 h, 88%; (v) (a) (5), triphosgene, CH₂Cl₂:THF (4:1), DIPEA, 0° C.-rt, 14h; (b) 3-Bromo-4-fluoroaniline, DIPEA, CH₂Cl₂, 0° C.-rt, 12 h, 56% (for both steps); (iv) 1-fluoro-4-isocyanato-2-(trifluoromethyl)benzene, CH₂Cl₂, rt, 48 h, 72%.

The synthesis of compound:

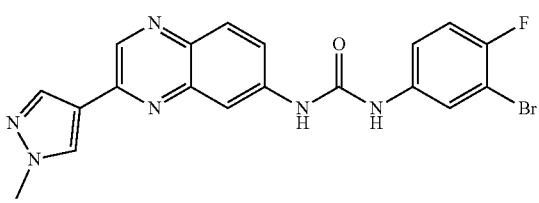 [SMILES: Cn1cc(-c2cnc3ccc(NC(=O)Nc4ccc(F)c(Br)c4)cc3n2)cn1]

(also termed 39-100) was performed by adding triphosgene (200 mg, 0.88 mol) in DCM (8 mL) at ° C. temperature. In another flask, compound 5 (PCT Int. Appl., WO 2011135376, 3 Nov. 2011.) was dispersed in THF (2mL) followed by addition of diisopropylethylamine (0.5 mL). Dispersed mixture was slowly added into the triphosgene solution at ° C. temperature. Maintained this temperature for about 1 h. 3-Bromo-4-fluoroaniline was added in to the reaction mixture and maintained 14 h at room temperature. Crude product was filtered and washed with DCM, MeOH and with HCl (0.1 M, 5mL) to remove the unreacted amine. Crude product was purified in MeOH and DCM, afforded yellow color product (252 mg, yield: 65%). The compound 39-100 was confirmed by NMR: ¹H NMR (499 MHz, DMSO-d₆) δ 9.48 (s, 1H), 9.26 (s, 1H), 9.11 (s, 1H), 8.60 (s, 1H), 8.35-8.13 (m, 2H), 8.04-7.85 (m, 2H), 7.68 (dd, J=2.4, 9.0 Hz, 1H), 7.50-7.19 (m, 2H), 3.94 (s, 3H). ¹³C NMR (126 MHz, DMSO) δ 152.91, 147.65, 142.96, 141.90, 141.61, 138.47, 137.44, 137.20, 131.45, 129.72, 122.97, 122.27, 120.57, 119.90, 119.84, 117.28, 117.09, 113.67, 108.24, 108.07, 39.38. ¹⁹F NMR (470 MHz, DMSO) δ -116.83.

The synthesis of compound:

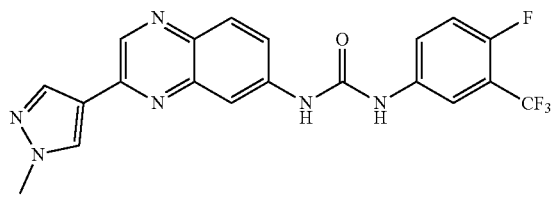 [SMILES: Cn1cc(-c2cnc3ccc(NC(=O)Nc4ccc(F)c(C(F)(F)F)c4)cc3n2)cn1]

(also termed 42-62) was performed by suspending this compound (50 mg, 0.22 mol) in DCM 1-fluoro-4-isocyanato-2-(trifluoromethyl) benzene was added and the reaction mixture stirred for 48 h at room temperature. The product was filtered and washed with DCM, hexane and dried under vacuum, obtained off-white colored product (68 mg, yield: 72%). The synthesis was confirmed by NMR: $^1$H NMR (499 MHz, DMSO-$d_6$) δ 9.74 (s, 1H), 9.12 (d, J=13.7 Hz, 2H), 8.62 (s, 1H), 8.48 (s, 1H), 8.28 (d, J=8.8 Hz, 2H), 7.95 (d, J=8.9 Hz, 1H), 7.65 (d, J=9.0 Hz, 1H), 7.40 (d, J=6.4 Hz, 2H), 3.95 (s, 3H). $^{13}$C NMR (126 MHz, DMSO) δ 155.23, 152.06, 147.39, 142.67, 142.42, 141.60, 140.70, 139.99, 139.92, 137.97, 136.82, 130.96, 129.40, 125.51, 125.00, 121.61, 120.17, 113.45, 79.15, 39.89. $^{19}$F NMR (564 MHz, DMSO) δ −119.00 (3F), −60.68 (1F).

Other compounds reported herein were prepared in a manner similar to the synthetic scheme shown for the above compounds.

Biological Assays

The activity of the compounds was assessed for inhibition of TNF alpha, and the results are shown in Table 2. Comparator compounds and their activity are reported in Table 2A.

TABLE 2

| ID# | TNFα induced NFκB transcription activity % Inhibition |
|---|---|
| 39-061 | 40.7 ± 2.9 |
| 39-055 | 71.0 ± 4.8 |
| 39-072 | 46.8 ± 4.4 |
| 39-062 | 33.0 ± 5.7 |
| 39-09D | 48.4 ± 2.8 |
| 39-077 | 37.7 ± 5.1 |
| 39-076 | 36.1 ± 8.8 |
| 39-071 | 31.2 ± 7.6 |
| 39-066 | 42.9 ± 9.8 |
| 39-085 | 53.0 ± 2.9 |
| 39-084 | 36.4 ± 6.3 |
| 39-086 | 88.9 ± 1.8 |
| 39-102 | 62.4 ± 1.2 |
| 42-064 | 96.3 ± 1.5 |
| 42-066 | Inactive |
| 42-071 | 80.5 ± 2.5 |
| 42-076 | 49.7 ± 2.6 |
| 42-81B | 60.9 ± 2.9 |
| 39-100 | 83.8 ± 1.6 |
| 42-062 | 83.7 ± 0.3 |
| 42-065 | 85.3 ± 2.8 |
| 42-074 | 10.4 ± 3.9 |
| 42-078 | 33.5 ± 3.7 |
| 42-096 | 64.6 ± 3.3 |

TABLE 2A

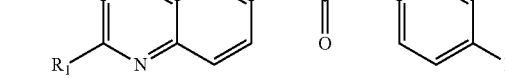

| ID# | —R$_1$ | —R$_2$ | TNFα induced NFκB transcription activity % Inhibition |
|---|---|---|---|
| 13-197 | 2-Furan | 2-Furan | 32.9 ± 3.4 |

| ID# | X | R | % Inhibition |
|---|---|---|---|
| 42-095 | C | Br | inactive |

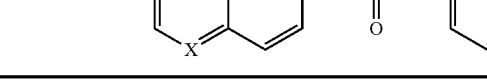

| ID# | R | % Inhibition |
|---|---|---|

TABLE 2A-continued

| | | |
|---|---|---|
| 42-072 | 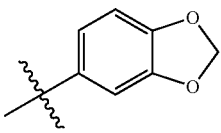 [SMILES: *c1ccc2c(c1)OCO2] | inactive |
| 42-073 | 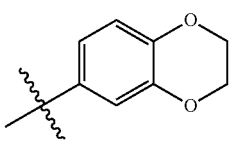 [SMILES: *c1ccc2c(c1)OCCO2] | inactive |
| 42-077 | 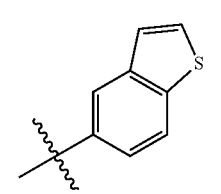 [SMILES: *c1ccc2sccc2c1] | inactive |
| 42-091 | 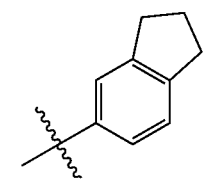 [SMILES: *c1ccc2c(c1)CCC2] | inactive |
| 42-097 | 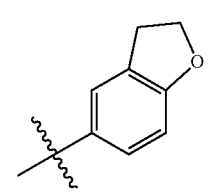 [SMILES: *c1ccc2c(c1)CCO2] | inactive |

Figure 1:
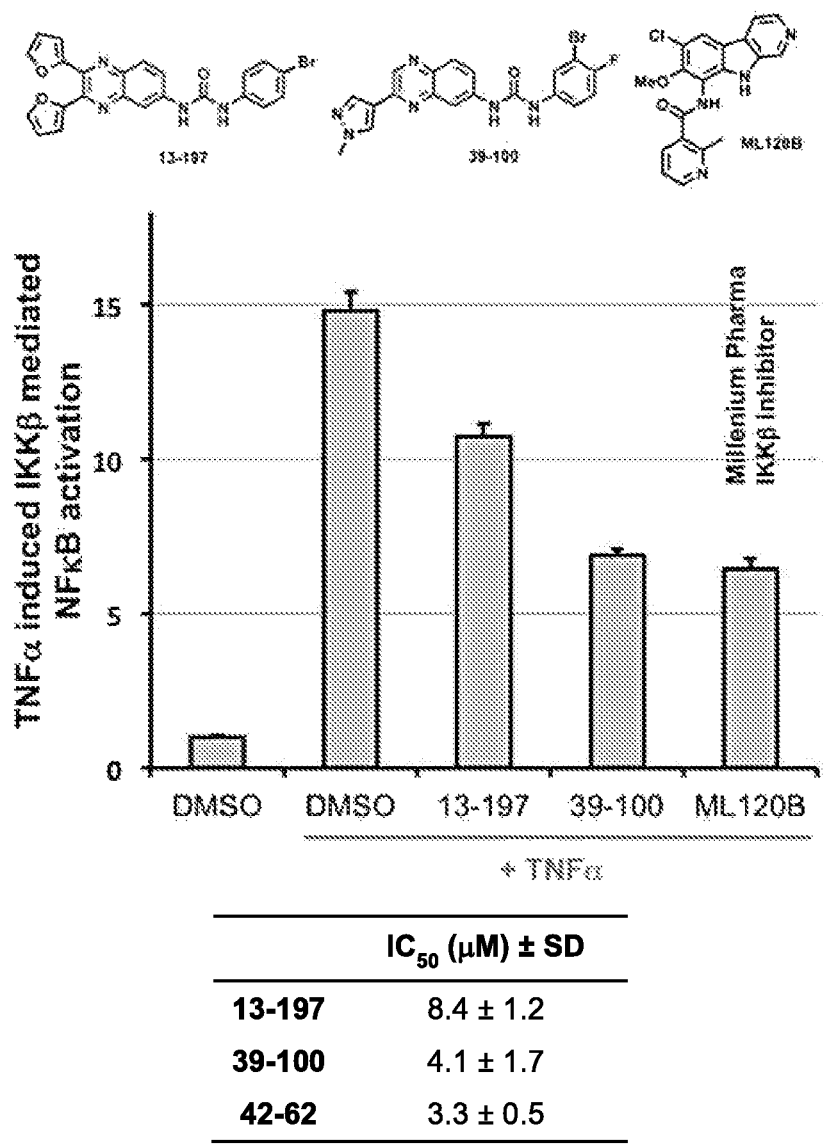
FIG. 1 shows the relative potency of compounds 13-197, 39-100 and ML-120B in a cell-based TNFα induced IKKβ mediated NFκB activation luciferase reporter assay. Compound 13-197 has a structure.

A systematic screening funnel identified compound 39-100 which is more potent than 13-197 in all the assays tested (FIG. 1 and FIG. 2). Table 3 below shows the growth inhibition assay of compound 39-100 in a panel of colon and pancreatic cancer cell lines. These data were obtained using an assay as reported in "*Targeting the NF-κB and mTOR pathways with a quinoxaline urea analog that inhibits IKKβ for pancreas cancer therapy*" Clin. Cancer Res. 2013, 19, 2025-2035.

TABLE 3

| | $GI_{50}$ (μM) | |
|---|---|---|
| Cell line | 13-197 | 39-100 |
| HCT116 | 8.8 ± 2.2 | 3.8 ± 1.2 |
| SW620 | 9.2 ± 2.5 | 8.4 ± 2.3 |
| HT29 | 6.7 ± 1.0 | 3.1 ± 0.2 |
| DLD1 | 10.9 ± 2.1 | 8.4 ± 2.3 |
| MiaPaCa2 | 10.0 ± 2.2 | 3.2 ± 0.3 |
| AsPC1 | 12.0 ± 4.0 | 7.2 ± 2.6 |
| Suit2 | 10.7 ± 0.5 | 4.5 ± 0.4 |
| S2013 | 9.1 ± 1.1 | 4.1 ± 0.5 |

A metabolic stability profile, as well as oral and intravenous dose pharmacokinetics in mice was characterized. The in-vitro metabolic stability of 39-100 was determined using human liver S9 fraction (XenoTech, LLC, USA). 7-hydroxycoumarin (glucuronidation and sulphation) and testosterone (CYP hydroxylation) were used as positive controls for in-vitro metabolic stability study. The oral and intravenous dose pharmacokinetic studies were performed in Balb/c mice. The oral dose of 39-100 was 10 mg/kg, and the intravenous dose was 1 mg/kg. Sample analysis was performed by liquid chromatography-tandem mass spectrometry (SCIEX QTRAP 4000 LC-MS/MS System). For metabolite identification, samples were acquired by MRM-information dependent acquisition-enhanced product ion (MRM-IDA-EPI) scans, enhanced mass spectrometry-IDA-EPI scans, neutral loss, and precursor ion scan methods. Metabolites of 39-100 were characterized by Analyst 1.6.2, LightSight 2.3.1, and ChemDraw Professional-15 software.

In human liver S-9 fraction, the half-life of 39-100 was observed 436.4 minutes, minutes and intrinsic clearance was 1.59 μl/min/mg protein. More than 85% of parent compound was present in human liver S9 fraction over 60-minute incubation (FIG. 3). In contrast, compound 13-197 was much less stable in vivo, with a half-life of 57 minutes and intrinsic clearance of 12.2 μL/min/mg protein.

In very small fraction glucuronidation, sulfonation, and demethylation of 39-100 was detected. The pharmacokinetic parameters of 39-100 after intravenous dose were determined as area under the curve ($AUC_{0-\infty}$)=597.5 ng·h/ml, elimination half-life ($t_{0.5}$)=3.9 h, clearance=1.67 L/h/kg, volume of distribution ($V_{ss}$)=2.4 L/kg, and mean residence time (MRT)=1.4 h. After oral administration, maximum plasma concentration ($C_{max}$) of 2328.3 ng/ml was observed after 2.0 h ($T_{max}$) of dose administration, $AUC_{0-\infty}$ was 12425.9 ng·h/ml, and MRT was 3.9 h. The oral bioavailability of 39-100 in mice was 208% (FIG. 4, Table 4). The oral bioavailability>100% is not a common phenomenon but it does take place sometimes. The possible reasons are nonlinear pharmacokinetics of the 10-times higher oral dose, which will inhibit intestinal efflux transporters, intestinal or liver metabolism, and/or biliary excretion.

TABLE 4

|  | IV: 1 mg/kg | Oral: 10 mg/kg |
| --- | --- | --- |
| $T_{max}$ (h) | NA | 2.0 |
| $C_0$-iv/$C_{max-oral}$ (ng/ml) | 709.9 | 2328.3 |
| $AUC_{last}$ (h*ng/mL) | 594.7 | 12413.4 |
| AUC0-∞ (h*ng/mL) | 597.5 | 12425.9 |
| $\lambda_Z$ (1/h) | 0.177 | 0.295 |
| $t_{0.5}$ (h) | 3.9 | 2.35 |
| CL/F (L/h/kg) | 1.67 | 0.80 |
| MRT 0-∞ | 1.4 | 3.9 |
| $V_{ss}$ (L/kg) | 2.4 | NA |
| Bioavailability (%) | NA | 208.00 |

Colon tumor xenografts were established in immune deficient (athymic: 4-6 weeks old) mice. Briefly, exponentially growing (70-80% confluent) HCT116 cancer cells were trypsinized, counted using a hemocytometer and stained with trypan blue to ensure only healthy cells are counted. Cells in suspension were added to matrigel and $4 \times 10^6$ cells/100 µl of volume were injected into the flanks of mice. Post-injection, mice were monitored on a daily basis to determine tumor growth. The tumor onset and progression was examined through palpation. Tumor diameter was measured using digital calipers and the tumor volume (in mm$^3$) was calculated using the formula=(width)$^2$×length/2. Mice were randomly separated into two groups and were dosed with either vehicle or 40 mg/kg of 39-100 for 2 weeks. Preliminary results indicate that 39-100 reduced colon tumor growth at 40 mg/kg dosing.

Compound 39-100 was tested in a pharmacodynamics study over a 4-week time period. 39-100 was compared to Gemcitabine and a control as shown in FIG. 6 and FIG. 7. study against Gemcitabine and a control. The Gemcitabine was administered to mice at 100 mg/kg every 4 days using intraperitoneal administration. The compound 39-100 was administered orally to mice at 40 mg/kg every 1 day.

What is claimed:

1. A compound, or pharmaceutically acceptable salt thereof, having a structure of formula (I):

(I)

wherein
 R$^1$ is H, halo, C$_{1-6}$ alkyl, C$_{1-6}$ haloalkyl, C$_{1-6}$ alkoxy, C$_{1-6}$ haloalkoxy, C$_{2-6}$ haloalkenyl, C$_{2-6}$ haloalkynyl, C$_{6-10}$ aryl or 5-7 membered heteroaryl having 1-4 ring heteroatoms selected from N, O, and S;
 one of R$^2$ and R$^{2a}$ is a 5-membered heteroaryl having 1-4 ring heteroatoms independently selected from N, O, and S, and optionally substituted with 1-4 R$^4$ groups, and the other one of R$^2$ and R$^{2a}$ is H;
 R$^3$ is H, halo, C$_{1-6}$alkyl, C$_{1-6}$ alkoxy, C$_{1-6}$ haloalkoxy, C$_{1-6}$haloalkyl, C$_{2-6}$haloalkenyl, or C$_{2-6}$haloalkynyl;
 each R$^4$ is independently halo, C$_{1-6}$ alkyl, C$_{1-6}$ haloalkyl, C$_{1-6}$ alkoxy, C$_{2-6}$ haloalkenyl, C$_{2-6}$ haloalkynyl, or C$_{6-10}$ aryl;
 any C$_{1-6}$alkyl or C$_{6-10}$aryl of R$^1$ and R$^4$ can optionally be substituted with 1-3 groups selected from halo, OH, C$_{1-6}$alkyl, C$_{1-6}$haloalkyl, CN, OC$_{1-6}$alkyl, CO$_2$H, and CO$_2$C$_{1-6}$alkyl; and
 with the proviso only one of R$^1$ and R$^3$ can be H.

2. The compound or salt of claim 1, wherein R$^1$ is halo or C$_{1-6}$alkyl.

3. The compound or salt of claim 1, wherein R$^1$ is F, Cl, Br, methyl, CF$_3$, methoxy, phenyl, furanyl, or thiophenyl.

4. The compound or salt of claim 1, wherein R$^2$ comprises furanyl, pyrazolyl, pyrollyl, oxazolyl, triazolyl, thiazolyl, or thiophenyl.

5. The compound or salt of claim 4, wherein R$^2$ is

6. The compound or salt of claim 1, wherein R$^2$ is substituted with 1 or 2 R$^4$ groups.

7. The compound or salt of claim 1, wherein R$^3$ is halo or C$_{1-6}$haloalkyl.

8. The compound or salt of claim 1, wherein at least one R$^4$ is F, Cl, methyl, methoxy, ethyl, or CF$_3$.

9. The compound or salt of claim 8, wherein at least one R$^4$ is methyl.

10. The compound or salt of claim 8, wherein at least one R$^4$ is CF$_3$.

11. The compound or salt of claim 1, having a structure selected from the group consisting of:

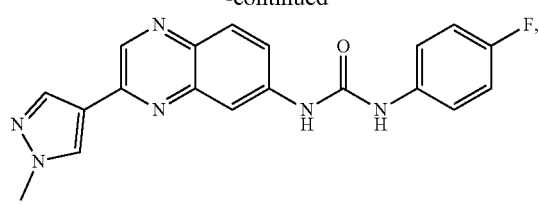
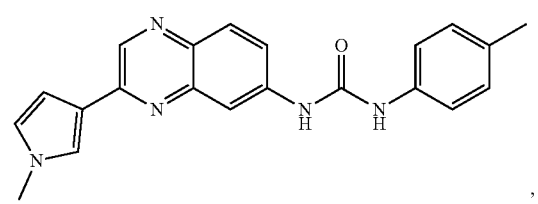
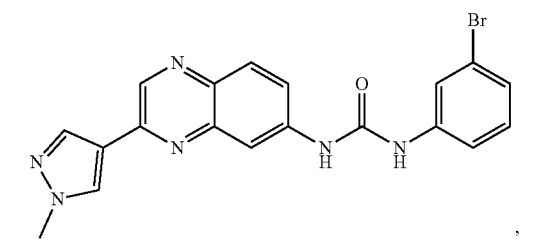
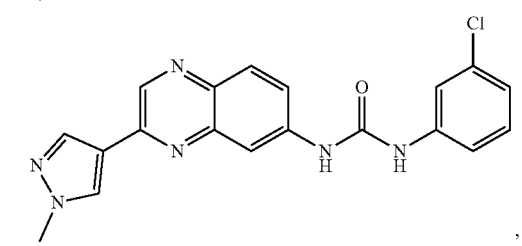
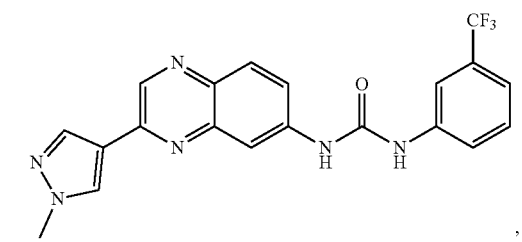
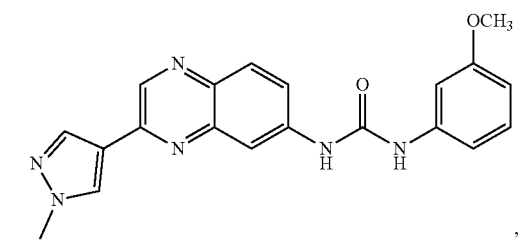
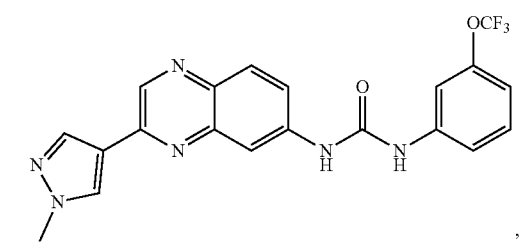
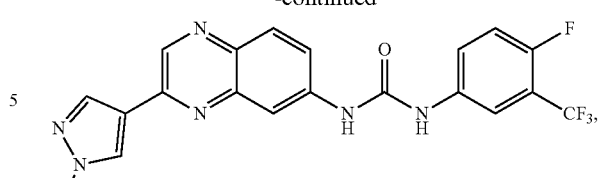
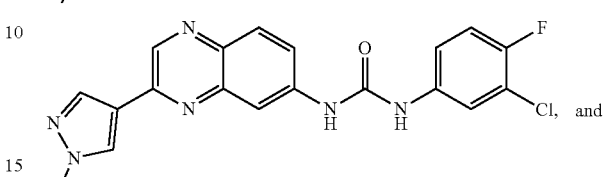
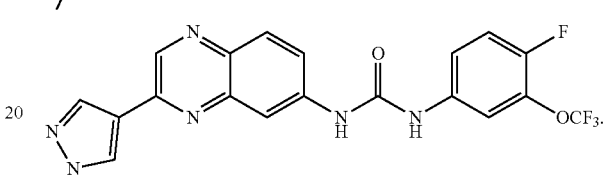
12. The compound or salt of claim 11, having a structure of
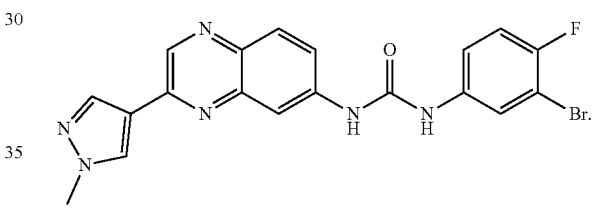
13. The compound of salt of claim 11, having a structure of
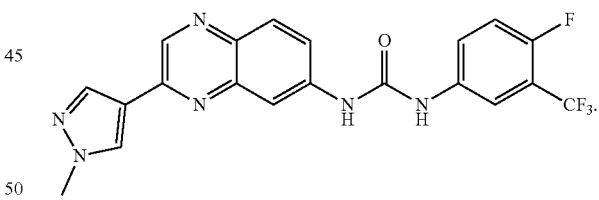
14. The compound or salt of claim 11, having a structure of
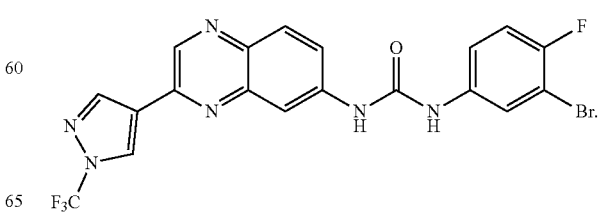

15. A compound, or pharmaceutically acceptable salt thereof, having a structure selected from the group consisting of:

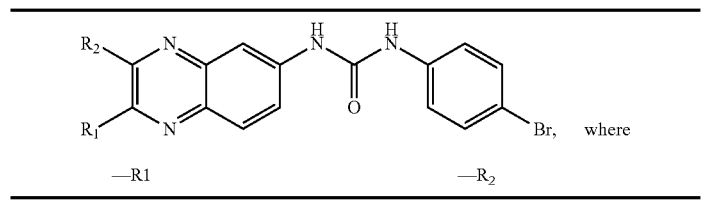

where

| —R1 | —R2 |
|---|---|
| 4-(1-methyl)-1H-Pyrazole | H, |
| H | 4-(1-methyl)-1H-Pyrazole, |
| 3-(1-methyl)-1 H-Pyrazole | H, |
| H | 3-(1-methyl)-1H-Pyrazole, |
| H | 4-1H-Pyrazole, or |
| H | 4-(1,3-dimethyl)-1H-Pyrazole; or |

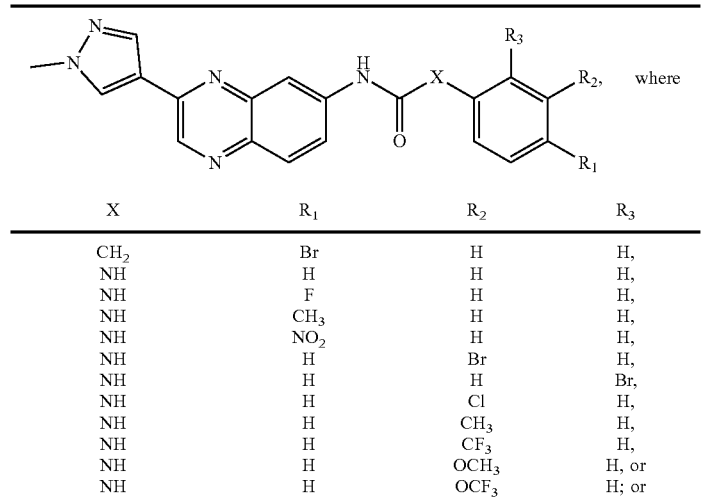

where

| X | R₁ | R₂ | R₃ |
|---|---|---|---|
| CH₂ | Br | H | H, |
| NH | H | H | H, |
| NH | F | H | H, |
| NH | CH₃ | H | H, |
| NH | NO₂ | H | H, |
| NH | H | Br | H, |
| NH | H | H | Br, |
| NH | H | Cl | H, |
| NH | H | CH₃ | H, |
| NH | H | CF₃ | H, |
| NH | H | OCH₃ | H, or |
| NH | H | OCF₃ | H; or |

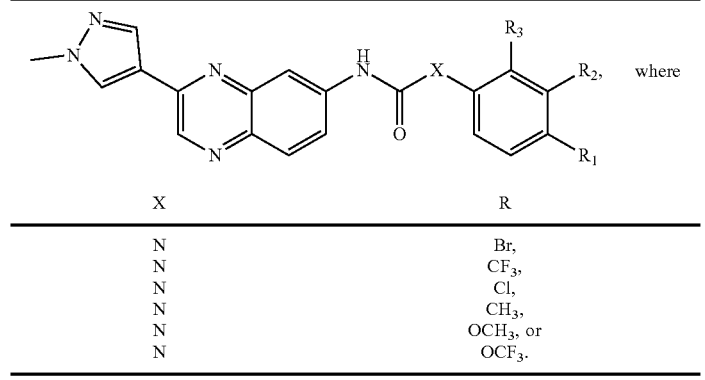

where

| X | R |
|---|---|
| N | Br, |
| N | CF₃, |
| N | Cl, |
| N | CH₃, |
| N | OCH₃, or |
| N | OCF₃. |

16. The compound or salt of claim 1, in the form of a salt.

17. A method of decreasing inhibitor of kappa B kinase β (IKKβ) activity in a cell comprising contacting the cell with the compound or salt of claim 1 in an amount effective to decrease activity of IKKβ or to decrease activity of IKKβ and decrease activity of NFκB.

18. A method of treating colon cancer or pancreatic cancer in a subject comprising administering to the subject a therapeutically effective amount of the compound or salt of claim 1, optionally wherein the compound or salt is administered orally.

* * * * *